(12) United States Patent
Jost (10) Patent No.: US 7,513,889 B2
(45) Date of Patent: Apr. 7, 2009

(54) DEVICE FOR DISPENSING AN INJECTABLE PRODUCT IN DOSES

(75) Inventor: Stefan Jost, Muehlberg (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/942,391

(22) Filed: Sep. 16, 2004

(65) Prior Publication Data

US 2005/0065477 A1    Mar. 24, 2005

(30) Foreign Application Priority Data

Sep. 19, 2003  (DE) ................. 103 43 548

(51) Int. Cl.
*A61M 5/00* (2006.01)
(52) U.S. Cl. .................... 604/207; 604/211
(58) Field of Classification Search ......... 604/207–211, 604/220, 134, 135.6, 187
See application file for complete search history.

(56) References Cited

U.S. PATENT DOCUMENTS

| | | | | |
|---|---|---|---|---|
| 4,883,472 A | * | 11/1989 | Michel | 604/208 |
| 5,626,566 A | * | 5/1997 | Petersen et al. | 604/208 |
| 5,957,896 A | * | 9/1999 | Bendek et al. | 604/207 |
| 6,193,698 B1 | * | 2/2001 | Kirchhofer et al. | 604/211 |
| 2002/0052578 A1 | * | 5/2002 | Moller | 604/208 |
| 2002/0111587 A1 | * | 8/2002 | Hommann et al. | 604/211 |
| 2005/0131355 A1 | * | 6/2005 | Kirchhofer et al. | 604/187 |
| 2005/0137571 A1 | * | 6/2005 | Hommann | 604/500 |

FOREIGN PATENT DOCUMENTS

| | | |
|---|---|---|
| DE | 10046279 A1 | 4/2002 |
| WO | 93/10839 A1 | 6/1993 |

* cited by examiner

*Primary Examiner*—Kevin C Sirmons
*Assistant Examiner*—Catherine N Witczak
(74) *Attorney, Agent, or Firm*—David E. Bruhn; Dorsey & Whitney LLP (57) ABSTRACT

A device for dispensing a product in doses including a casing element, a dosing device shiftable relative to the casing element in a dispensing direction, a setting device for setting the position of the dosing device, and a restoring element for returning the dosing device to a starting position, wherein a movement of the dosing device in the dispensing direction charges the restoring element.

15 Claims, 6 Drawing Sheets

DEVICE FOR DISPENSING AN INJECTABLE PRODUCT IN DOSES

BACKGROUND

The invention relates to devices and methods for dispensing, including devices and methods for dispensing, administering, injecting and/or infusing a medicinal product, including injectable medicinal products, such as insulin or hormone preparations, in doses. The application claims the priority of German patent application No. 103 43 548.4, filed on Sep. 19, 2003 with the German Patent and Trademark Office.

Devices for dispensing, administering or injecting injectable products are well-known. Such devices may include a dosing means, some of which are restorable or resettable, but it may be difficult to restore the dosing means and, in some cases, it may not be possible at all.

EP 0 614 386 B1 describes a device in which a toothed rack which acts on a piston arranged in a container for the dosing product is only provided with teeth over a part of its circumference. The teeth of the toothed rack cooperate with opposing teeth in such a way that the toothed rack can be shifted in discrete increments for the purpose of delivering the product but is prevented from being simply retracted. In order to be restored, the toothed rack is formed such that the teeth and the opposing teeth are disengaged by rotating the toothed rack by 90° and the toothed rack can then be manually retracted and moved to a starting position for a new, dosed delivery. Restoring the driven member requires the user to perform a number of movements in coordination. This, however, can lead to problems for a user who is perhaps not familiar with handling a somewhat complex mechanism, and therefore restrict the range of application of the device.

A device for administering an injectable product in doses is known from DE 10 046 279 A1, belonging to the Applicant, wherein a restoring spiral spring is provided which is secured when tensioned and is coupled to a drive unit by a release and can cause a restoring movement of the drive unit towards its dosing starting position.

SUMMARY

It is an object of the present invention to provide a device for dispensing an injectable product in doses, in which it is possible to automatically restore or reposition a dosing device. In particular, the intention is to provide such a device in which a restoring element can be used in a number of restoring procedures and wherein the restoring element can be integrated into the device in a way which conserves as much space as possible.

This object is addressed by providing a device for dispensing a product in doses comprising a casing element, a dosing device which can be shifted relative to the casing element, a setting device using which the position of the dosing device can be set, and a restoring element which uses a movement of the dosing device in a dispensing direction to generate a restoring force by which the dosing device can be returned to a starting position.

In accordance with one embodiment of the present invention, the device for dispensing an injectable product, such as insulin or hormone preparations, in doses comprises a casing element or a mechanism holder which can accommodate component parts of a dosing mechanism or the complete dosing mechanism. A dosing device, for example a threaded rod, is mounted such that it can be shifted relative to the casing element and preferably in the casing element. An ampoule containing the injectable product to be dosed can be connected to the casing element and a particular amount of the substance contained in the ampoule can be dosed or selected for dispensing by shifting the dosing device relative to the casing element. The selected amount is then dispensed by actuating a triggering button. The position of the dosing device can be set or altered using a setting device, which, for example, can be rotated relative to the dosing device and/or casing element. A restoring element is provided in or on the device and can generate a restoring force which can automatically return the dosing device to its starting position (or another selected position) again after one or more dosing procedures, for example, to exchange a partially or completely emptied ampoule and replace it with a new, filled ampoule. In one embodiment the restoring element is preferably formed and arranged such that the force required to restore the dosing device is accumulated during a setting and/or dispensing procedure of the device and the force thus accumulated can be transferred to the dosing device after the restoring element has been released, in order to move it to a starting position.

In one embodiment, the present invention comprises a device for dispensing a product in doses including a casing element, a dosing device shiftable relative to the casing element, a setting device for setting the position of the dosing device, and a restoring element for returning the dosing device to a starting position, wherein a movement of the dosing device in the dispensing direction charges or loads the restoring element.

The "dosing device" is to be understood to be a device for adjusting, setting or selecting the amount of a substance to be dispensed or injected, including from an ampoule or other container. It should also be understood that it is possible for the dosing device to also be used to dispense the substance, e.g., by shifting the dosing device.

In one embodiment, the restoring element is preferably a spring element such as a helical spring or a spiral spring which can be compressed by moving the dosing device in the dispensing direction and thus accumulates the force required to restore the dosing device. Using a helical spring is advantageous since it can be integrated into a dispensing device without a great need for space, for example by being arranged around a threaded rod or the like used as the dosing device. Additional, separate elements do not then have to be attached to the dispensing device, which simplifies the design of the dispensing device. In one embodiment, the restoring spring element is advantageously arranged coaxially with the dosing device, the casing element and/or at least partially within the casing element. In some embodiments, the restoring or spring element generates a force in an axial direction of the casing element and/or in the movement direction of the dosing device by being arranged, for example, between the dosing device and the casing element itself or between the dosing device and an element which can be inserted into the casing element, such as, for example, a sealing part as described below.

In some embodiments, including in preferred embodiments, a safety mechanism is provided which prevents the dosing device from being restored or moved by the restoring element. This safety mechanism can, for example, be a switch or a rotational block such as described below.

In some embodiments, a threaded engagement is preferably provided between the setting device and the dosing device, wherein the setting device is preferably arranged coaxially with the dosing device. The setting device can, for example, have an inner thread which can be engaged with the dosing device which for example is formed by a threaded rod with an outer thread. It is equally possible for the setting device to comprise an outer thread which can be engaged with an inner thread of the dosing device.

If the dosing device comprises a thread which engages with a corresponding thread of the setting device, then it is advantageous to form the thread such that it is not self-locking, i.e., the thread pitch should be chosen such that the force applied to the dosing device by the restoring element is sufficient to move the dosing device towards a starting position.

In one preferred embodiment, the dosing device can be secured against rotation relative to the casing element, during a dosing procedure, dispensing procedure, or other operation by the dosing device exhibiting a rotationally asymmetrical cross-section, such that a passage opening corresponding to the cross-section and arranged in an element which is mounted secured against rotation relative to the casing element can hold the dosing device in the casing element, secured against rotation. The dosing device can then still be freely moved through the this rotational block. If the element serving as the rotational block for the dosing device is released relative to the casing element, then the dosing device can also be moved and, in particular, rotated relative to the casing element. When the dosing device is secured against rotation, the position of the dosing device can then be altered by rotating the setting device coupled to the dosing device via a thread, in order to set a dosage of the substance to be dispensed for example from an ampoule. Advantageously, the setting device can be rotated relative to the casing element.

Advantageously, in some embodiments, the setting device can be secured against rotation relative to the casing element and the dosing device can preferably be freely moved, in particular rotated, relative to the casing element when the setting device is secured against rotation. This enables the restoring element provided in accordance with the invention to return or retract the dosing device to a starting position, e.g., once the restoring element has been released. The dosing device can be coupled to the setting device via a threaded engagement, in which case the dosing device is screwed back when restored to the starting position by the force of the restoring element. It is equally possible for the threaded engagement to be released, which enables the dosing device to be returned to the starting position by the force generated or provided by the restoring element, in which position the setting device is coupled to the dosing device again by rotating the dosing device and/or the restoring device in order to re-establish a threaded engagement between these two devices. Other suitable coupling arrangements and coupling/decoupling operations could be used to engage the devices.

In one embodiment, the rotational blocks of the dosing device and the setting device are preferably coupled such that in a first state the setting device can be freely moved and the dosing device is secured against rotation and, in a second state the dosing device can be freely moved and the setting device is secured against rotation. The term "secured against rotation" is to be understood as a holder, mounting structure or shape of the device in question which prevents said device from rotating relative to another device acting on said device. Thus, for example, in the case of a threaded engagement rotating one device coupled to the device secured against rotation causes the device secured against rotation to not rotate with the one device but to convert the rotational force into an advancing or retracting movement.

In accordance with another embodiment and/or effect of the present invention, the invention relates to a system comprising a device as described above and a coupling device for an ampoule, into which an ampoule can be inserted or plugged or to which an ampoule can be connected generally, wherein the dosing device can be inserted into the interior of the ampoule, for example during or after the setting procedure, in order to displace a substance in the ampoule, the amount of the substance dispensed from the ampoule being determined by the insertion depth of the dosing device.

In one embodiment, the ampoule coupling device is advantageously configured such that when an ampoule is plugged onto the dispensing device or connected to the dispensing device, the dosing device is secured against rotation and can be moved into or towards the ampoule by rotating the setting device. If the ampoule coupling is not coupled or connected to an ampoule, the rotational block on the dosing device is advantageously released, enabling the dosing device to be rotated back to a starting position by the restoring element.

DETAILED DESCRIPTION

Figure 1:
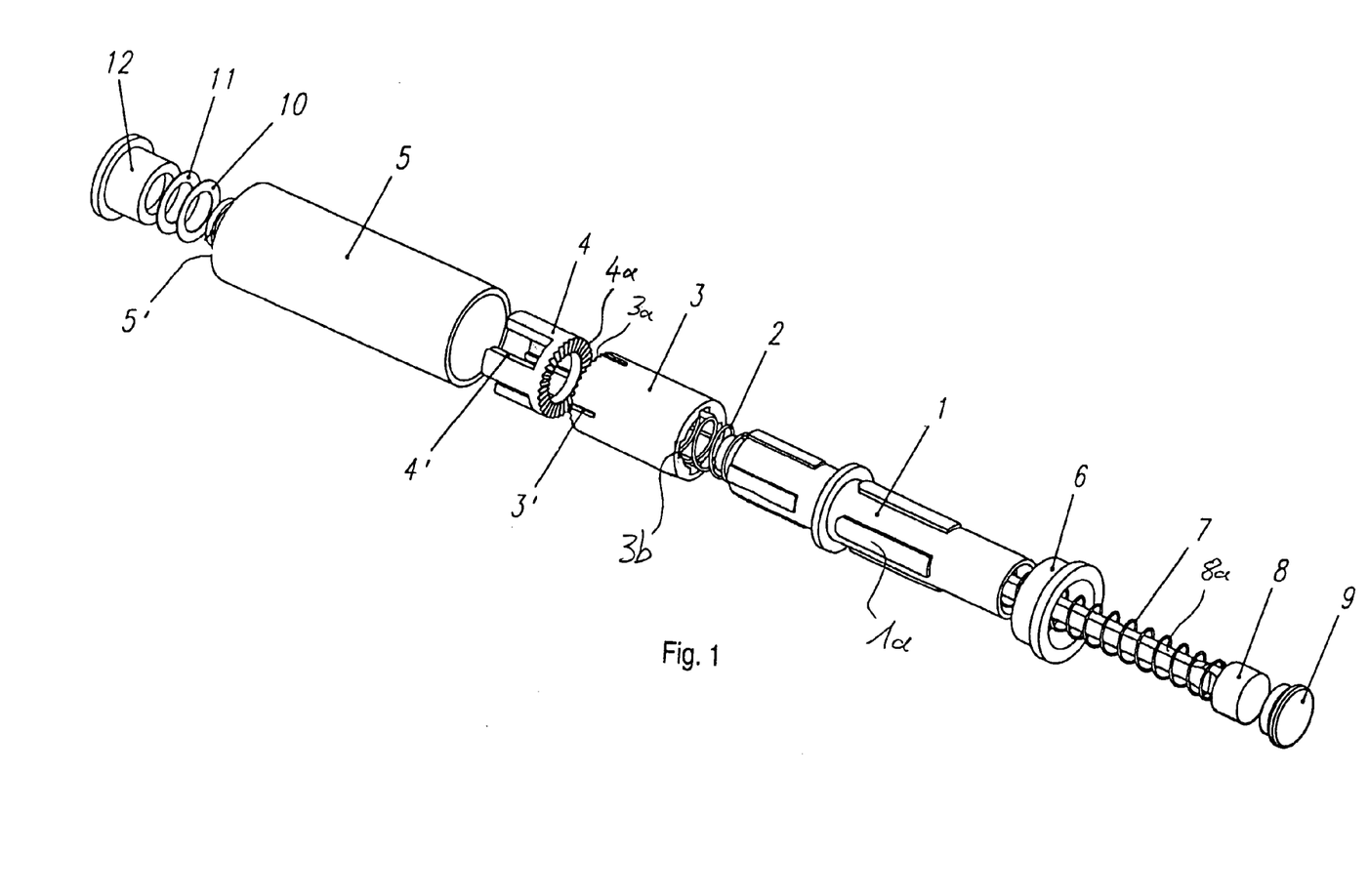
FIG. 1 depicts an embodiment of the device in accordance with the invention, in an exploded view.
Figure 3:
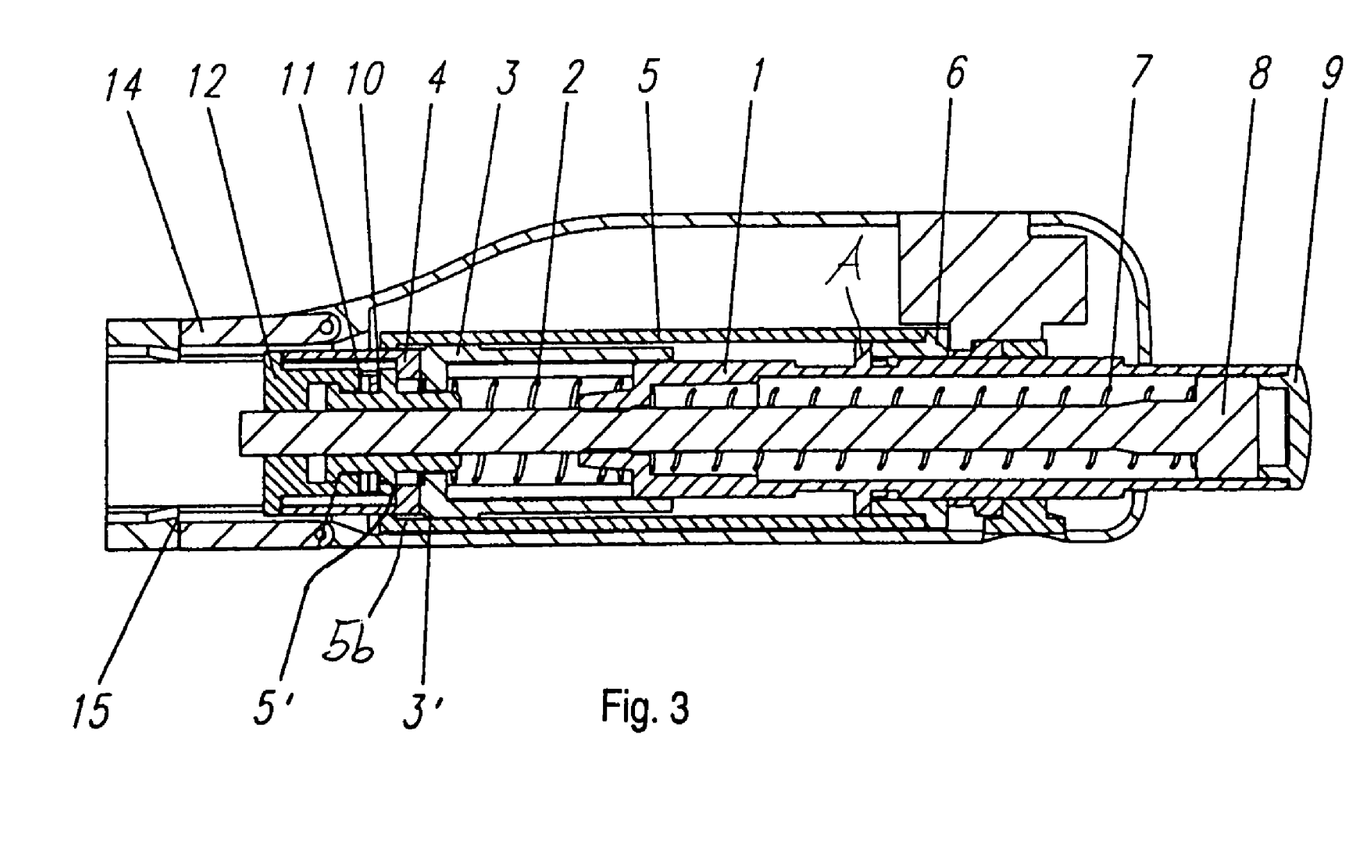
FIG. 3 is a cross-sectional view of the device shown in FIG. 1, assembled in the starting position.
Figure 4:
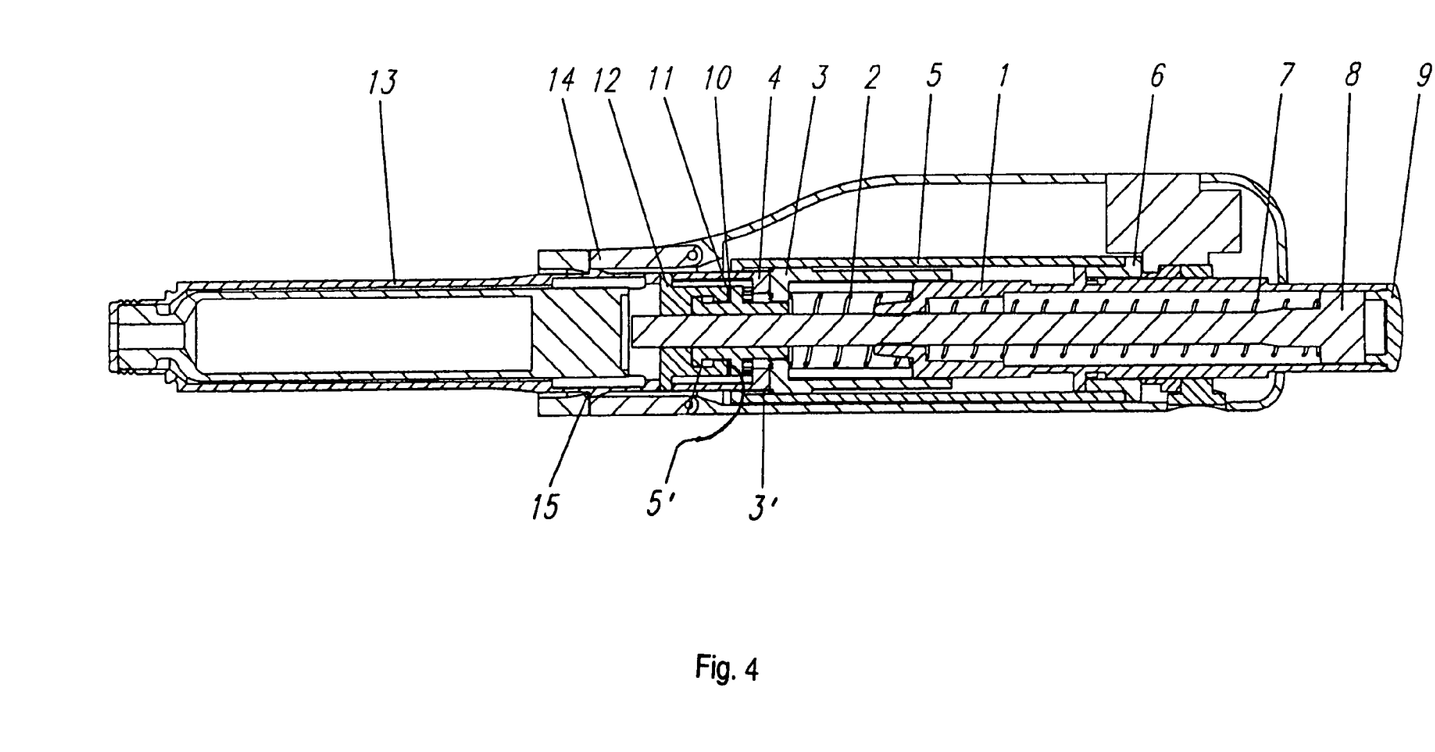
FIG. 4 depicts the device shown in FIG. 3, with an ampoule sleeve attached, in the starting position.

FIG. 1 shows an embodiment of a device in accordance with the present invention, comprising a mechanism holder 5 which serves as the casing element and comprises a stopper 5' at its front end, shown on the left in FIG. 1, an abrasive disc 10 being attached to said stopper. An abrasive disc 11 is arranged opposite the abrasive disc 10 and is fastened on a rotating ring 12. When assembled as shown in FIG. 3, the abrasive discs 10 and 11 do not lie on each other and are not loaded with a pressure additionally acting from without, e.g., by an ampoule as shown in FIG. 4, such that the rotating ring 12 can be rotated relative to the mechanism holder 5. The threaded rod exhibits a threaded profile 8a on the upper side shown in FIGS. 1 and 2 and on the lower side (not shown) and is flattened on the front side shown in FIG. 1 and on the opposite side, such that the threaded rod 8 can be guided in a mounting or passage opening 12a of the rotating ring 12 shown in FIG. 2, which approximately corresponds to the cross-section of the threaded rod 8, enabling the threaded rod 8 to be mounted in the rotating ring 12, secured against rotation.

In the embodiment shown, the mechanism holder 5 comprises four passages 5a through which the insertion elements 4' of the releasing part 4 can be guided in order to be able to connect the releasing part 4 to the mechanism holder 5 or insert the releasing part 4 into the mechanism holder 5 secured against rotation.

A grating 4a is provided on the surface of the releasing part 4 facing away from the insertion elements 4' of the releasing part 4 and can engage with a corresponding grating 3a of the sealing part 3 when the sealing part 3 and the releasing part 4 are abutting or lying on each other, which couples the sealing part 3 and the releasing part 4 such that a rotation can be transferred. The pressure spring 2 arranged between the threaded nut 1 and the sealing part 3 causes the sealing part 3 and the releasing part 4 to tend to always be lying on each other when assembled as shown in FIG. 3.

The threaded nut comprises tappets 1*a* which engage with cavities 3*b* of the sealing part 3 and so establish a rotational block between the threaded nut 1 and the sealing part 3. An inner thread 1*b* is provided in the interior of the threaded nut 1 and can engage with the outer thread 8*a* of the threaded rod 8, such that the threaded rod 8 mounted in the rotating ring 12, secured against rotation, can be moved in the axial direction of the device, e.g., to the left in the representation shown in FIG. 1, by rotating the threaded nut 1.

In the starting position shown in FIG. 3, the sealing part 3 is mounted, secured against rotation, in corresponding grooves 5*b* of the mechanism holder 5, via tappets 3'.

Figure 2:
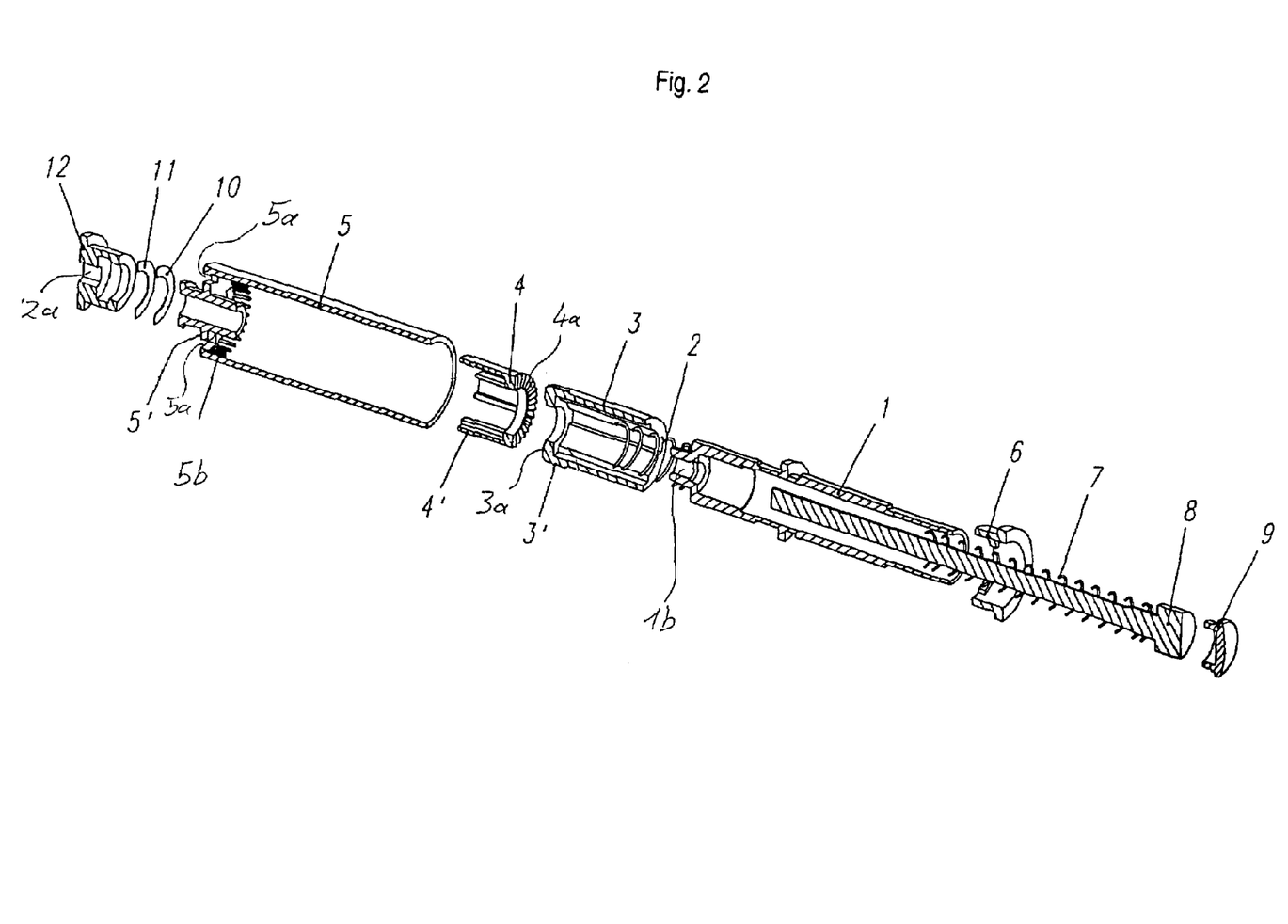
FIG. 2 depicts the device of FIG. 1, cut open in the longitudinal direction.

A helical spring 7 serving as a restoring element is arranged at the rear end of the threaded rod 8, shown on the right in FIG. 2, and when assembled is bounded or contacted on one side by the head of the threaded rod 8 and on the other side by an inner stopper of the threaded nut 1.

A mechanism lock 6 and a dosing button cap 9 seal the mechanism and can serve as end stoppers.

In the starting position (shown in FIG. 3), the releasing part 4 and the sealing part 3 are inserted far enough into the mechanism holder 5 for the tappets 3' provided as the rotational block to engage with the corresponding grooves 5*b* of the mechanism holder 5. In this position, the sealing part 3 cannot be rotated relative to the mechanism holder 5 and the threaded nut 1 held together with the sealing part 3 via the tappets 1*a* which engage with the cavities 3*b* of the sealing part 3 is likewise secured against rotation relative to the mechanism holder 5. In the starting position shown in FIG. 3, the threaded rod 8 is in a rear position and can be rotated relative to the mechanism holder 5, since the abrasive discs 10 and 11 lie unloaded on each other. The threaded rod 8 is thus pushed backwards far enough so no force acting backwards is applied to the threaded rod 8 by the helical spring 7, which could shift the threaded rod 8 even further backwards.

Figure 5:
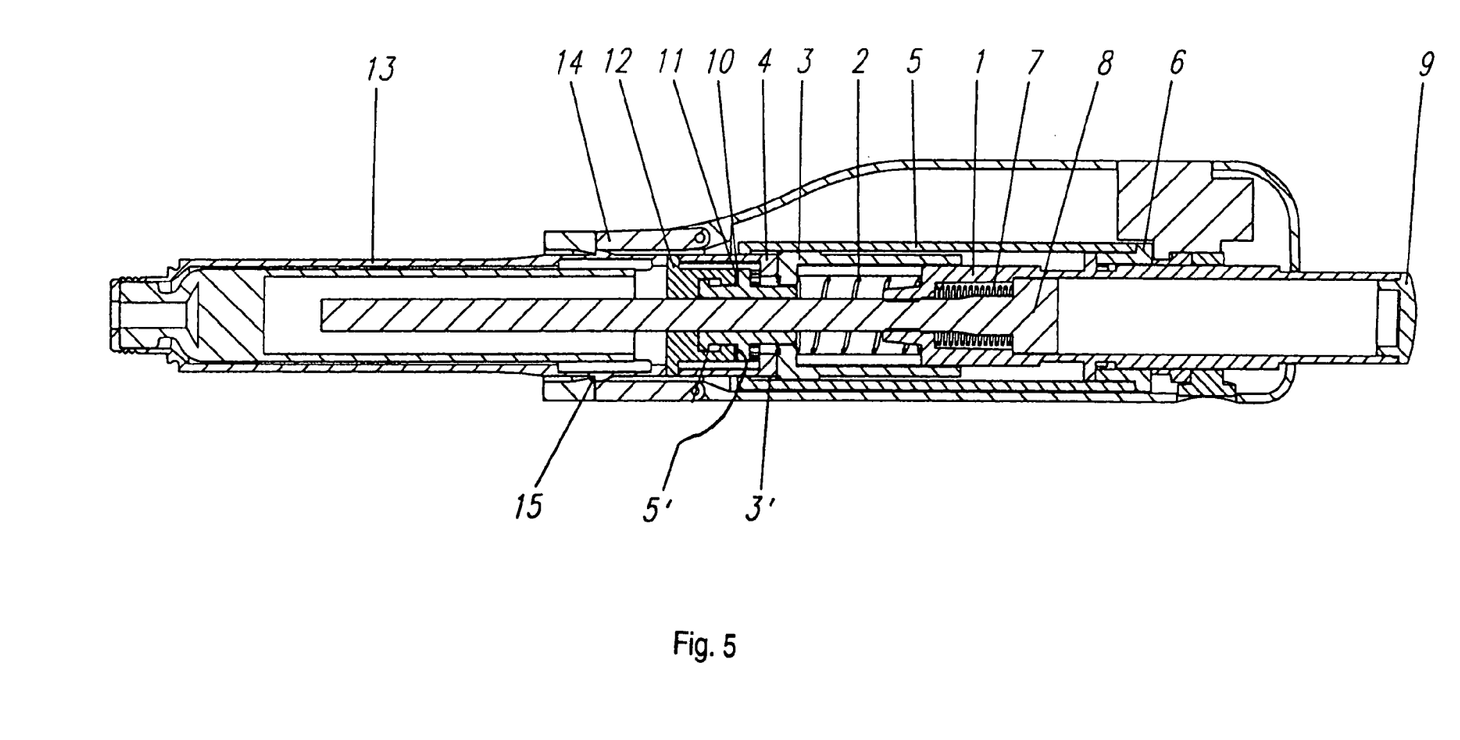
FIG. 5 depicts the device shown in FIG. 4, with the threaded rod extended.
Figure 6:
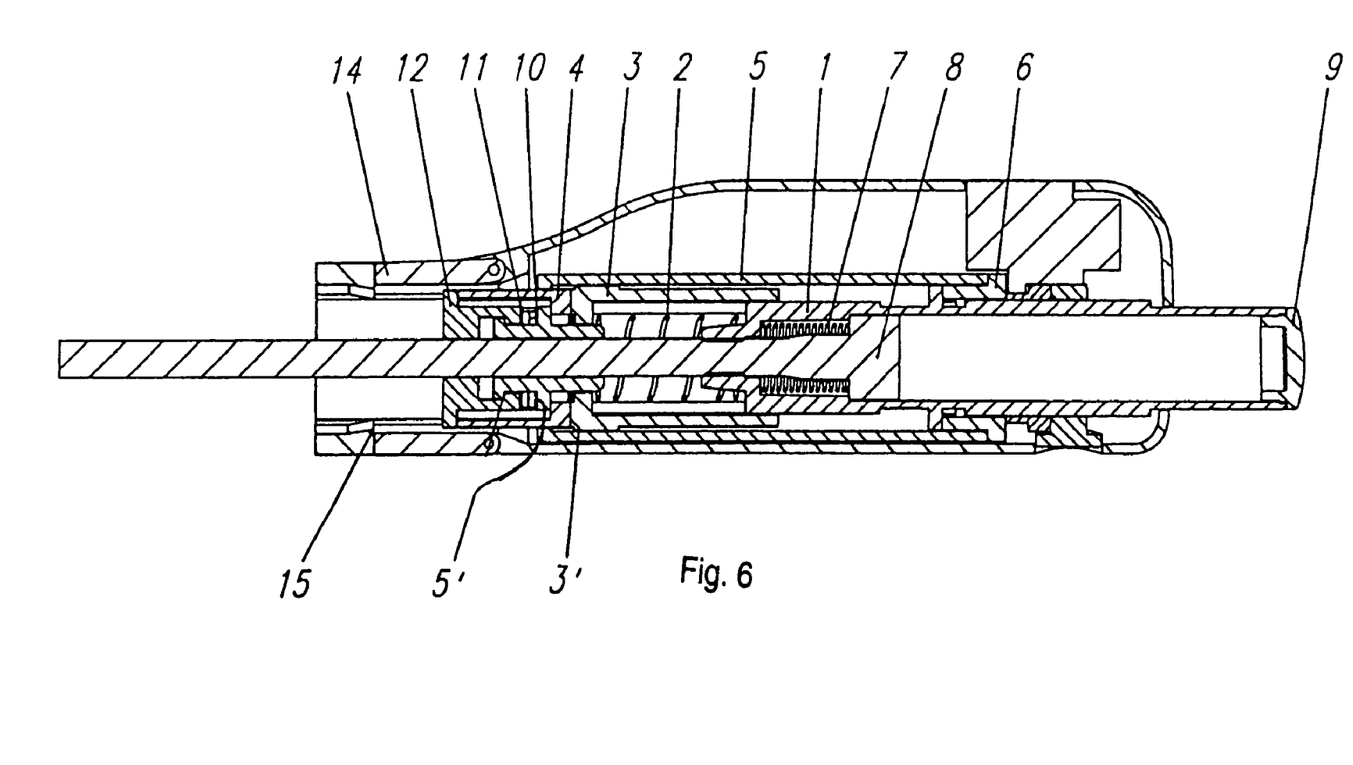
FIG. 6 depicts the device shown in FIG. 5, after the ampoule has been removed.

If an ampoule sleeve 13 is plugged onto the device as shown in FIG. 3, then the ampoule sleeve 13 snaps in at the undercut 15 as shown in FIGS. 4 and 5. The rotating ring 12 is pushed backward—to the right in FIG. 3—such that the abrasive discs 10 and 11 are lying on each other and couple the rotating ring 12, secured against rotation, to the mechanism holder 5, which also secures the threaded rod 8, mounted in the passage opening 12*a*, against rotation. Furthermore, the insertion elements 4' of the releasing part 4 are pushed through the passages 5*a* of the mechanism holder 5, which likewise pushes the releasing part 4 backwards together with the sealing part 3. The sealing part 3 is pushed backwards far enough for the tappets 3' (serving as the rotational block with respect to the mechanism holder 5) to be pushed out of the corresponding grooves 5*b* of the mechanism holder 5, enabling the sealing part 3 to be rotated relative to the mechanism holder 5. This releases the threaded nut 1, coupled to the sealing part 3, relative to the mechanism holder 5, which can then be rotated.

Rotating the threaded nut 1 leads to an axial movement of the threaded rod 8, via the inner thread 1*b* which is coupled to the outer thread 8*a* of the threaded rod 8 now mounted, secured against rotation, by the rotating ring 12 which is secured against rotation. By continuing to rotate the threaded nut 1, the threaded rod 8 can be shifted towards the ampoule sleeve 13 until the threaded rod 8 is in a front position as shown in FIG. 5, in which the maximum volume to be displaced or dispensed from the ampoule is set. The helical spring 7 arranged around the threaded rod 8 is maximally biased by shifting the threaded rod 8.

A dispensing procedure is triggered or actuated by pressing the dosing button cap 9, which presses the threaded rod 8—which is extended forward in accordance with the desired dosage—onto a displacement body in the ampoule 13 by which the substance stored in the ampoule is displaced and output from an ampoule opening, e.g., to be injected.

If the ampoule has been sufficiently emptied that it needs to be exchanged, then the threaded rod 8 is situated in a front position as shown in FIG. 5. If the ampoule sleeve 13 is released from the device in accordance with the invention by means of a pressure device 14, then the front pressure spring 2 pushes the sealing part 3, the releasing part 4 and the rotating ring 12 forwards again. Thus, the sealing part 3 is secured against rotation via the tappets 3' which engage with the corresponding grooves 5*b* of the mechanism holder 5, and the threaded nut 1 is secured against rotation again.

Shifting the rotating ring 12 forwards releases the abrasive disc 11 from the abrasive disc 10, i.e., the abrasive discs 10, 11 no longer lie on or contact each other due to an external force, which leaves the rotating ring 12 free and no longer secured against rotation, such that the threaded rod 8, mounted in the rotating ring 12 in the mounting 12*a*, can likewise be rotated. The helical spring 7 pressing onto the threaded rod 8 causes the threaded rod 8 to be rotated back in the axial direction of the device, as far as its starting position shown in FIG. 3. It is thus no longer necessary, when exchanging an ampoule, for a user to manually rotate the threaded rod 8 back, which simplifies the handling of the device in accordance with the invention.

Instead of the coupling or operable connection formed by the abrasive discs 10 and 11, other coupling systems can also be used. Examples include a laminar coupling formed by a number of abrasive discs, a tapered abrasive coupling formed by tapered sleeves, a sinusoidal laminar coupling formed, for example, by a bent spring metal sheet, or a coupling formed by disc springs, etc.

In the foregoing description, embodiments of the present invention, including preferred embodiments, have been presented for the purpose of illustration and description. They are not intended to be exhaustive or to limit the invention to the precise steps and forms disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for dispensing a product in doses, comprising a casing element, a coupling device for releasably receiving an ampoule sleeve arranged at a front end of the casing element, a dosing device shiftable relative to said casing element from a starting position to a front position for dosing medicament from the ampoule sleeve, a setting device for setting the position of said dosing device, a front pressure spring arranged at the front end of the casing element for releasing a locking engagement of said dosing device against movement towards the starting position, and a spring element effectively acting between the setting device and the dosing device and provided at a rear end of the casing element, and wherein upon release of the locking engagement of the dosing device, the spring element using a movement of the dosing device towards the front position and away from a rear end of the setting device to generate a restoring force by which the dosing device can be returned to the starting position such that the ampoule sleeve may be released without manual resetting of the dosing device.

2. The device as set forth in claim 1, wherein the spring element is either a helical spring or a spiral spring.

3. The device as set forth in claim 1, wherein the spring element is arranged around the dosing device.

4. The device as set forth in claim 1, wherein the spring element is arranged substantially coaxially with at least one of the casing element, said setting device and the dosing device.

5. The device as set forth in claim 1, further comprising a safety mechanism which prevents the dosing device from being restored by the spring element.

6. The device as set forth in claim 1, wherein a threaded engagement is provided between the setting device and the dosing device.

7. The device as set forth in claim 1, wherein the setting device comprises an inner thread and the dosing device comprises an outer thread.

8. The device as set forth in claim 1, further comprising a rotational block for securing the dosing device against rotation relative to the casing element.

9. The device as set forth in claim 1, further comprising a rotational block for securing the setting device against rotation relative to the casing element.

10. The device as set forth in claim 1, further comprising a first rotational block for securing the dosing device against rotation relative to the casing element and a second rotational block for securing the setting device against rotation relative to the casing element.

11. The device as set forth in claim 10, wherein said first rotational block and said second rotational block are coupled such that in the starting position, the setting device can be rotated and the dosing device is secured against rotation, and in the front position the setting device is secured against rotation and the dosing device can be rotated.

12. The device as set forth in claim 10, wherein at least one of the rotational blocks for the setting device and the dosing device can be established or released by said coupling device.

13. The device as set forth in claim 1, wherein the coupling device is a pressure device.

14. A device for dispensing a product in doses comprising:
a casing element;
a coupling device for releasably receiving an ampoule sleeve arranged at a front end of the casing element;
a dosing device shiftable relative to the casing element from a starting position to a front position for dosing medicament from the ampoule sleeve;
a setting device for setting the position of the dosing device;
a releasable locking engagement of said dosing device arranged at the front end of the casing element, the releasable locking engagement for securing said dosing device against movement towards the starting position, wherein a front pressure spring is arranged at the front end of the casing element for releasing the locking engagement of said dosing device against movement towards the starting position; and
a spring element effectively acting between the setting device and the dosing device and provided at a rear end of the casing element, and wherein upon release of the locking engagement of the dosing device, the spring element using a movement of the dosing device towards the front position and away from a rear end of the setting device to generate a restoring force by which the dosing device can be returned to the starting position such that the ampoule sleeve may be released without manual resetting of the dosing device.

15. A device for dispensing a product in doses comprising:
a casing element;
a coupling device for releasably receiving an ampoule sleeve arranged at a front end of the casing element;
a dosing device comprising a threaded rod shiftable relative to the casing element from a starting position to a front position for dosing medicament from the ampoule sleeve;
a setting device comprising a threaded nut for setting the position of the dosing device;
a releasable locking engagement of said threaded rod arranged at the front end of the casing element, the releasable locking engagement for securing said threaded rod against movement towards the starting position, wherein a front pressure spring is arranged at the front end of the casing element for releasing the locking engagement of said threaded rod against movement towards the starting position; and
a spring element effectively acting between the threaded nut and the threaded rod and provided at a rear end of the casing element, and wherein upon release of the locking engagement of the threaded rod, the spring element using a movement of the threaded rod towards the front position and away from a rear end of the setting device to generate a restoring force by which the threaded rod can be returned to the starting position such that the ampoule sleeve may be replaced without manual resetting of the threaded rod.

* * * * *